United States Patent [19]

Bachman

[11] Patent Number: 4,931,774
[45] Date of Patent: Jun. 5, 1990

[54] LIQUID-VAPOR CHANGE OF PHASE DETECTOR

[75] Inventor: Wesley J. Bachman, Auburn, Ill.

[73] Assignee: DICKEY-john Corporation, Auburn, Ill.

[21] Appl. No.: 233,065

[22] Filed: Aug. 17, 1988

[51] Int. Cl.$^5$ ............................................. G08B 21/00
[52] U.S. Cl. ..................... 340/603; 340/583; 340/604; 250/573; 250/574; 250/577; 73/DIG. 11; 73/61.1 R; 73/53; 356/437
[58] Field of Search ......... 340/603, 604, 583; 250/573, 574, 577; 356/463, 437; 73/DIG. 11, 61.1 R, 53

[56] References Cited

U.S. PATENT DOCUMENTS

| 3,544,798 | 4/1968 | Topol | 250/573 |
| 4,212,005 | 7/1980 | Hubert | 340/603 |
| 4,251,809 | 2/1981 | Cheney | 340/603 |
| 4,631,529 | 12/1986 | Zeitz | 250/573 |
| 4,816,695 | 3/1989 | Lavin | 250/573 |

Primary Examiner—Joseph A. Orsino
Assistant Examiner—Kinfe-Michael Negash
Attorney, Agent, or Firm—Richard Bushnell

[57] ABSTRACT

An apparatus for detecting a liquid-vapor change of phase in a fluid substance traveling through a conduit comprises a detector housing providing a path of travel for fluid and interposed in a portion of the fluid-carrying conduit in which the change of phase is to be detected, a source of radiation disposed for directing radiation into the path of travel and a detector for detecting radiation disposed generally at an opposite side of the path of travel from the said source. The arrangement is such that radiation from the source will pass through the fluid in the path of travel prior to reaching the detector. The detector is responsive to radiation detected thereat for producing a corresponding electrical signal. A detector circuit is responsive to the electrical signal produced by said detector for producing an output signal indicative of a liquid-vapor change of phase of the fluid in the conduit.

6 Claims, 1 Drawing Sheet

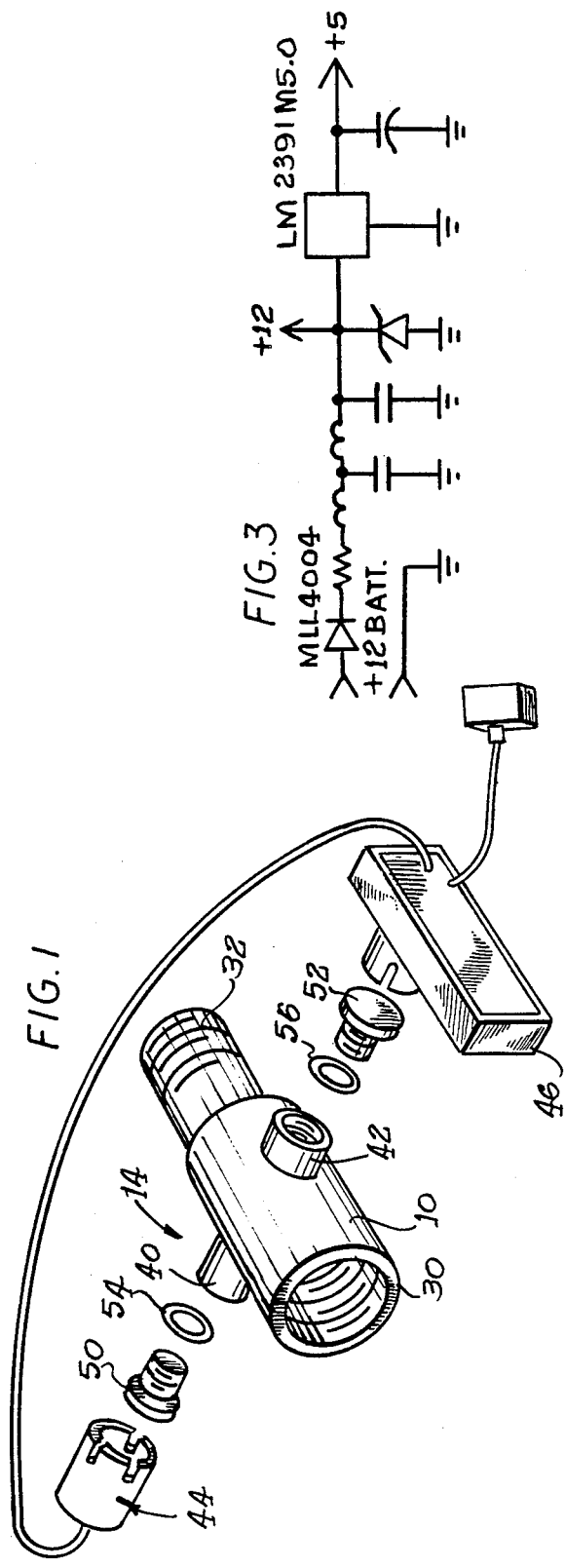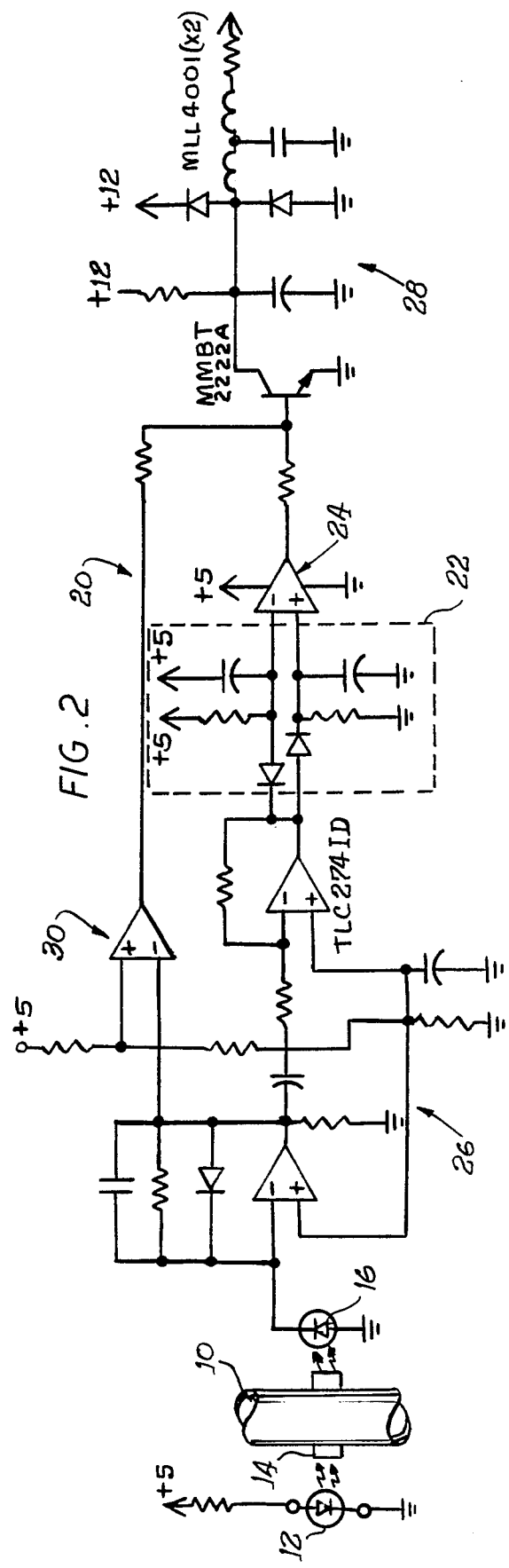

LIQUID-VAPOR CHANGE OF PHASE DETECTOR

BACKGROUND OF THE INVENTION

This invention is directed generally to the monitoring of a flow of fluid, such as anhydrous ammonia (NH3), and more particularly to a novel apparatus for detecting a change, in the flowing fluid, from the liquid to the vapor phase.

Anhydrous ammonia (NH3) is extensively used as a fertilizer material in agriculture. Moreover, in relatively large-scale mechanized agriculture, relatively expensive and complex machinery is utilized to apply anhydrous ammonia to cultivated fields. This equipment is made somewhat more complex by the necessity of providing for proper and safe handling of anhydrous ammonia, including relatively large tanks for storage of a supply of the material, and well-sealed tubing, valves, metering devices and the like to carefully control the application thereof.

The anhydrous ammonia is most commonly applied by a so-called "knife", comprising a narrow blade-like implement which generally opens a narrow furrow or kerf and applies the anhydrous ammonia into the recently opened furrow through a narrow tube behind the blade. A plurality of such knives are generally provided in parallel, spaced sets on an elongate frame which is pulled by a suitable implement for applying material at the desired density.

It is important in such operations to keep track of the amount of fertilizer material applied, usually on a pounds per acre or some other weight or volume per area basis. In order to provide such metering of the flow of anhydrous ammonia, it is necessary to provide a flow metering device and a flow control device in line with the supply of anhydrous ammonia, and preferably prior to branching out to the one or more knives at which the material is applied. However, in order to accurately control and monitor the flow of anhydrous ammonia, the material must be in a liquid phase or state. That is, conventional flow meters and flow control devices are generally designed to operate with liquid materials rather than gaseous materials. Accordingly, all NH3 closed loop control systems employ some thermal exchange device in an effort to achieve a liquid phase at the metering point.

In general, systems for measuring the flow of this material assume that the metering or measurement area or volume is fixed and this volume is also assumed to be fully occupied by a flowing stream of liquid at all times. That is, a continuous or steady state situation is assumed. It is further usually assumed that the thermal exchange device has reliably provided substantially 100% liquid state material by converting any and all vapor into the liquid state just prior to the metering point.

However, it is apparent that any heat exchanger and/or other system of practical size and cost will only operate to convert a given proportion (i.e., less than 100%) of vapor to liquid at a given temperature. Beyond this practical limit, some vapor will pass through the flow meter resulting in some proportionate error in the measurement of flow.

While the power rating for a given heat or thermal exchanger is readily determinable, this information is not particularly useful in actual NH3 application operations. Rather, the primary matter of interest is maintaining the maximum vehicle speed over the ground consistent with maintaining the desired application density of the material. In large scale farming operations, it is important to optimize all operations, which in turn requires that a maximum speed of operation be attained in passing over the field for planting, fertilizing and cultivation procedures.

In theory, a maximum flow rate should be predictable, once one has determined a system's static and thermal losses. However, such losses depend upon the length, diameter, and condition of the piping and hosing on a given applicator, the existence and condition of couplers and valves, the condition of a supply tank and attendant plumbing and the nominal pressure and temperature of the supply tank, as well as knife injection pressure. These static and thermal system losses are therefore extremely difficult to predict and/or measure.

Moreover, it has been determined that even the thermal energy differences encountered from relatively bright sunlight as opposed to overcast days may be significant in effecting the thermal losses of a given thermal or heat exchanger. Accordingly, since energy losses per unit time are not readily predictable, the power rating of a given exchanger is not useful in determining the maximum flow capacity for a given anhydrous (NH3) application system. Thus, most operators must determine this from an essentially trial and error basis and by almost continuous observations to determine the actual maximum operating flow condition and hence optimum speed of operation with a given system. Needless to say, with relatively complex agricultural machinery, continuous observation by a single operator of not only the operating flow rates, but also the many other parts of the equipment which may require observation and checking, is a most difficult, if not an impossible proposition.

In order to remedy this situation, some systems have proposed various temperature differential measurements across the thermal exchanger and/or the monitoring of frequency output variations of a flow meter. While such methods are in theory workable, in practice the response times of such systems have proven much too long to provide any but a relatively coarse result, and greatly delayed corrections. That is, with these systems, a sufficient time lag exists between the onset of the undesirable condition (i.e., excessive anhydrous ammonia in vapor phase) and a reliable indication of the condition, that the actual correction is only made after an improper rate of distribution has been in effect for some while.

We have found that surprisingly improved results may be obtained by visually observing the flow of NH3 through a section of transparent pipe in the vicinity of the flow meter. We have recognized that confined NH3 has an equilibrium temperature and pressure that must be physically satisfied at all times if the liquid phase is to be maintained. Moreover, we have found that the formation of vapor bubbles is readily observable for even minute deviations of temperature or pressure from the equilibrium point. Moreover, this bubble formation or "boiling" occurs almost instantaneously upon variation of the fluid temperature and pressure from this equilibrium point. Accordingly, we have discovered a very useful detection mechanism which gives a nearly zero time lag between onset of this undesirable condition and the onset of observable effects thereof.

We have further discovered that since the dielectric constant of liquid NH3 is generally 20 to 40 times greater than that of its vapor state, these bubbles are readily discernible by the use of electromagnetic waves in or near the visible spectrum. Accordingly, we have chosen to use readily available infrared radiation producing and detecting devices to monitor the flow of a stream of NH3 in a section of tubing or a fitting placed relatively near the flow metering point in the system. However other forms of radiation, e.g., ultrasonics, might also be used without departing from the invention in its broader aspects.

OBJECTS AND SUMMARY OF THE INVENTION

It is therefore a general object of the invention to provide a radiation-based detection system for detecting the existence of vapor phase bubble formation in a flow of liquid anhydrous material, and for providing a usable output signal indicative of the same.

Briefly, and in accordance with the foregoing objects, apparatus for detecting a liquid-vapor change of phase in a fluid substance traveling through a conduit comprises detector housing means providing a path of travel for said fluid and interposed in a portion of the fluid-carrying conduit in which said change of phase is to be detected; a source of radiation disposed for directing radiation into said path of travel; detector means for detecting radiation disposed generally at an opposite side of said path of travel from said source, such that radiation from said source will pass through the fluid in the path of travel prior to reaching said detector means; said detector means being responsive to radiation detected thereat for producing a corresponding electrical signal; and detector circuit means responsive to said electrical signal produced by said detector means for producing an output signal indicative of a liquid-vapor change of phase of the fluid in the conduit.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

FIG. 1 is an exploded perspective view of a liquid to vapor state change detector apparatus in accordance with the invention;

FIG. 2 is a diagram in circuit schematic form of a detector circuit useful with the apparatus of FIG. 1; and FIG. 3 is a circuit schematic diagram of a power supply circuit for the circuit of FIG. 2.

DETAILED DESCRIPTION OF THE ILLUSTRATED EMBODIMENT

Referring now to the drawings, and initially to FIGS. 1 and 2, apparatus for detecting a liquid-vapor change of phase in a fluid substance traveling through a conduit comprises a detector housing means or member 10 which provides a path of travel for the fluid and is interposed in a portion of the fluid-carrying conduit (not shown) in which the change of phase is to be detected. A source of radiation such as a light emitting diode (LED) 12 is disposed generally adjacent the housing means 10 for directing radiation into the path of travel therethrough. To this end, the housing means 10 is preferably provided with a suitable fitting or other means 14 which is, at least in part, transparent to the radiation produced by the source of radiation and, in the embodiment illustrated herein transparent to radiation in the infrared range produced by LED 12.

A detector means or detector of radiation, such as an infrared sensitive diode 16 ("photodiode") or other similar transducer is placed at an opposite side of the path of travel from the source of radiation 12, such that the radiation from the source must pass through the fluid in the path of travel provided by housing 10 in order to reach the detector 16. The light sensitive diode or detector means 16 is responsive to the infrared electromagnetic radiation which reaches it for producing a corresponding electrical signal.

Cooperatively, a detector circuit or circuit means 20, comprising the remaining portion of FIG. 2, is coupled in circuit for receiving this electrical signal produced by the detector means or diode 16 and is responsive thereto for providing a usable electrical signal for indicating a change of phase in the fluid flowing through the housing 10. Preferably, this circuit means includes a differential peak detector circuit portion 22 which is coupled in circuit for providing a peak value signal corresponding to a peak value of the electrical signal produced at the transducer or detector means 16.

In the preferred form of the detector circuit 20 shown in FIG. 2, the differential peak detector circuit portion 22 has a suitable time constant and operates into an open loop difference amplifier 24. Accordingly, it will be seen that the peak detector will provide a peak value signal corresponding generally to a peak value of the electrical signal produced by the detector or photodiode 16. The coupling with the difference amplifier results in the production of an output signal which will undergo an abrupt change in level in response to the peak value signal reaching or exceeding a predetermined level.

In operation, upon the formation of vapor bubbles in the fluid flowing through the conduit and in particular, in detector housing 10, a rapid change in the peak signal level produced by the detector 16 will immediately occur. This in turn will cause an abrupt change in output level from amplifier 24 so as to indicate the presence of bubbles to any downstream alarm, control or other device which may be coupled in circuit with the output of amplifier 24. That is, since the bubbles will tend to scatter the light, the receiver or photodiode 16 will see a changing light level as a bubble or bubbles pass.

Preferably, a further band pass amplifier circuit 26 is interposed between the detector or photodiode 16 and the differential peak detector circuit 22. This will amplify the signal received at the differential peak detector and limit the pass band so as to focus on the desired detector signal and eliminate much of the background noise and other unwanted electrical interference. Accordingly, this circuit operates essentially to produce a "noise"]output signal from detector 16 when bubbles pass through the conduit 10 and this "noise" signal is amplified, peak detected and, if above a certain level triggers an abrupt change in level of the output of amplifier 24.

This abrupt change of level can be used to trigger or turn on other downstream equipment to form a suitable alarm, to drive a meter or give other suitable indication of the presence of bubbles, and hence the start of a change from liquid to vapor state of the NH3. Preferably, the pass band of band pass amplifier circuit 26 is on the order of 16 hertz to about 20 kilohertz. This approximate upper frequency will be defined essentially by the additional stray capacitance of this circuit, and is not a particularly critical limit.

Preferably, the infrared source is a light emitting diode of the type generally designated XL880C and the detector is a photodiode of the type generally designated SFH205 (Siemens). In the illustrated embodiment, an additional output buffer amplifier circuit 28 is utilized to effectively buffer and interface the illustrated circuit from downstream circuitry, meters, alarms or other devices which the circuit is intended to operate in a given installation.

We have also found that in some instances severe turbulence in the flow can cause undue blockage of the light reaching the detector 16. Also, buildup of dirt, dust or other contaminants can sometimes block the otherwise transparent windows through which the radiation must pass to reach the detector 16. Accordingly, we have added to the illustrated preferred embodiment an additional feed forward loop in the form of a DC comparator circuit 30. This DC comparator circuit has its output ORed to the output of difference amplifier 24 at the input of buffer 28. Accordingly, this circuit is now capable of providing warning for either of two vaporization conditions, either the existence of undesired vapor in the liquid NH3 flow or the indication of a non-operative state due to excessive turbulence or foreign material blockage.

Turning now more particularly to FIG. 1, other features of the apparatus in accordance with the invention are illustrated therein. It will be seen that the housing 10 comprises a tubular, open-ended member which has couplings or coupling means at respective ends thereof for interfitting with a fluid-carrying conduit, In the illustrated embodiment, the coupling means 30, 32 comprise respective pipe threads such that the housing may be readily threaded in series in a conduit formed of similar pipe-threaded conduit members. Respective fittings or fitting means 40, 42 are located at generally diametrically opposed sides of the housing and are generally in diametrically opposed alignment with a transverse section through the housing. These fittings provide areas for mounting the LED 12 and photodiode 16, respectively.

In this regard, the photodiode 16 and LED 12 are preferably potted or otherwise enclosed in suitable environmentally protective housings of plastics material designated generally by reference numerals 44 and 46. These housings 44 and 46 in turn are adapted to removably interfit over the respective fittings 40 and 42, in order to permit disassembly of these members for cleaning, if and as necessary.

Additional mating fitting members 50, 52 are additionally provided which in turn receive the respective housings 44, 46 and interfit, preferably through mating machine screw threads, with fittings 40, 42. Preferably, additional sealing means such as rubber O-rings or grommets 54, 56, are sealingly engaged between the respective fittings 40, 42 and 50, 52. These latter fittings 50, 52 are also constructed at least in part of a material which is transparent to the form of radiation utilized, and in the illustrated embodiment, this is electromagnetic radiation the infrared or near-visible spectrum. Accordingly, the fittings 50, 52 in effect define windows to the interior of the housing for said radiation to leave the LED and enter the photodiode, respectively.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. Apparatus for detecting a liquid-vapor change of phase in a fluid substance traveling through a conduit comprising: detector housing means providing a path of travel for said fluid and interposed in a portion of the fluid-carrying conduit in which said change of phase is to be detected; a source of radiation disposed for directing radiation into said path of travel; detector means for detecting radiation disposed generally at an opposite side of said path of travel from said source, such that radiation from said source will pass through the fluid in the path of travel prior to reaching said detector means; said detector means being responsive to radiation detected thereat for producing a corresponding electrical signal; and detector circuit means responsive to said electrical signal produced by said detector means or producing an output signal indicative of a liquid-vapor change of phase of the fluid in the conduit; wherein said detector circuit means comprises differential peak detector means coupled in circuit for receiving said electrical signal produced by said detector means and responsive thereto for providing as outputs two peak value signals corresponding to peak values of said electrical signal, difference amplifier means coupled to receive the outputs of said differential peak detector means and responsive thereto for producing an output signal which undergoes an abrupt change in level in response to the peak value signal reaching or exceeding a predetermined level and buffer amplifier means for receiving and buffering the output of said difference amplifier means.

2. Apparatus according to claim 1 wherein said detector circuit means further comprises band pass amplifier circuit means coupled intermediate said detector means and said differential peak detector means for band limiting and amplifying said electrical signal from the detector means to provide an amplified signal having an improved signal-to-noise ratio to said differential peak detector circuit means.

3. A detector circuit for use with an apparatus for detecting a liquid-to-vapor change of phase in a fluid flowing through a conduit and including transducer means for producing an electrical signal as an analog of the flow of fluid through said conduit, wherein said change of phase of fluid produces a distinct change in a characteristic detectable by said transducer means and a corresponding distinct change in the electrical signal produced thereby, said detector circuit comprising: differential peak detector means coupled in circuit with said transducer means and responsive to said electrical signal for producing two peak level signals corresponding to peak levels of the electrical signal produced by said transducer means, and difference amplifier means coupled to receive said peak level signals and responsive thereto for producing an output signal which undergoes an abrupt change in level in response to the level of said peak detector signals reaching or exceeding a predetermined level; and further including buffer amplifier means for receiving and buffering the output of said difference amplifier means.

4. A detector circuit according to claim 3 and further including ban pass amplifier means coupled intermediate said transducer means and said differential peak detector circuit means for band limiting and amplifying the electrical signal produced by said transducer means so as to provide a signal having improved signal-to-noise characteristics to said differential peak detector means.

5. Apparatus for detecting a liquid-vapor change of phase in a fluid substance traveling through a conduit comprising: detector housing means providing a path of travel for said fluid and interposed in a portion of the fluid-carrying conduit in which said change of phase is to be detected; a source of radiation disposed for directing radiation into said path of travel; detector means for detecting radiation disposed generally at an opposite side of said path of travel from said source, such that radiation from said source will pass through the fluid in the path of travel prior to reaching said detector means; said detector means being responsive to radiation detected thereat for producing a corresponding electrical signal; detector circuit means responsive to said electrical signal produced by said detector means for producing an output signal indicative of a liquid-vapor change of phase of the fluid in the conduit; said detector circuit means comprising differential peak detector means coupled in circuit for receiving said electrical signal produced by said detector means and responsive thereto for providing peak value signals corresponding to peak values of said electrical signal, band pass amplifier circuit means coupled intermediate said detector means and said differential peak detector means for band limiting and amplifying said electrical signal from the detector means to provide an amplified signal having an improved signal-to-noise ratio to said differential peak detector circuit means, and a loop circuit portion comprising a DC level comparator circuit means coupled intermediate said amplifier circuit means and an output of said difference amplifier means for providing a further signal at said output means indicative of a non-operative state of said conduit due to blockage by foreign material or the like.

6. A detector circuit for use with an apparatus for detecting a liquid-to-vapor change of phase in a fluid flowing through a conduit and including transducer means for producing an electrical signal as an analog of the flow of fluid through said conduit, wherein said change of phase of fluid produces a distinct change in a characteristic detectable by said transducer means and a corresponding distinct change in the electrical signal produced thereby, said detector circuit comprising: differential peak detector means coupled in circuit with said transducer means and responsive to said electrical signal for producing two peak level signals corresponding to peak levels of the electrical signal produced by said transducer means, and difference amplifier means coupled to receive said peak level signals and responsive thereto for producing an output signal which undergoes an abrupt change in level in response to the level of said peak detector signals reaching or exceeding a predetermined level; band pass amplifier means coupled intermediate said transducer means and said differential peak detector circuit means for band limiting and amplifying the electrical signal produced by said transducer means so as to provide a signal having improved signal-to-noise characteristics to said differential peak detector means, and a loop circuit portion comprising a DC level comparator circuit means coupled intermediate said amplifier circuit means and an output of said difference amplifier means for providing a further signal at said output means indicative of a non-operative state of said conduit due to blockage by foreign material or the like.

* * * * *